United States Patent [19]

Sternberg

[11] 4,372,683
[45] Feb. 8, 1983

[54] PHOTOMETER WITH ROTATING SAMPLE CONTAINER

[75] Inventor: James C. Sternberg, Fullerton, Calif.

[73] Assignee: Beckman Instruments, Inc., Fullerton, Calif.

[21] Appl. No.: 300,419

[22] Filed: Sep. 9, 1981

Related U.S. Application Data

[63] Continuation of Ser. No. 71,813, Sep. 4, 1979, abandoned.

[51] Int. Cl.³ .................... G01N 21/47; G01N 21/84
[52] U.S. Cl. ................................. 356/338; 356/244; 356/427; 356/440; 435/291
[58] Field of Search ............... 356/338, 339, 427, 428, 356/436, 440, 244; 250/576

[56] References Cited

U.S. PATENT DOCUMENTS 4,136,953  1/1979  Klein et al. ................. 356/339
4,157,871  6/1979  Anderson et al. ........... 356/338 X

FOREIGN PATENT DOCUMENTS 909038  10/1962  United Kingdom ............ 356/436
678396   8/1979  U.S.S.R. ...................... 356/426

*Primary Examiner*—Vincent P. McGraw
*Attorney, Agent, or Firm*—R. J. Steinmeyer; Robert R. Meads; John R. Shewmaker

[57] ABSTRACT

Photometric analysis apparatus having a cylindrical glass sample container which is rotated about its axis during optical measurement of sample in the container. Rotation of the 5 container window areas past an optical detector compensates for optical variations and imperfections in the container wall which would otherwise render the measured photometric signal sensitive to each particular rotational orientation of the container.

3 Claims, 2 Drawing Figures

PHOTOMETER WITH ROTATING SAMPLE CONTAINER

This is a continuation, of application Ser. No. 071,813, filed Sept. 4, 1979, now abandoned.

BACKGROUND OF THE INVENTION

1. Field of the Invention

The present invention relates to the photometric assay of sample material and, more particularly, to the optical assay of sample in containers subject to optical variations or imperfections.

2. Description of the Prior Art

U.S. Pat. No. 4,136,953 (Klein et al.) and U.S. Pat. No. 4,157,871 (Anderson et al.) disclose nephelometric systems for the assay of antigens and antibodies supported within cylindrical glass containers. In such analysis, an antigen and an antibody are combined in the container and the resulting reaction between these sample components produces a precipitate which increases in quantity and turbidity as the reaction progresses. An excitation system directs a beam of light into the container and a detection system measures light scattered at a designated angle by the precipitate. The light scattered by the precipitate is a function of its turbidity and is employed to derive quantitative or qualitative information about the antigen or antibody sample components.

The above-mentioned Anderson et al. patent discloses a system employing kinetic methods for measuring the change in scatter during an early part of the antigen antibody reaction and for deriving the maximum rate of change of the scattered light to assay the sample components. Using this approach the measurement can be completed rapidly in less than one minute without waiting for the reaction to proceed to completion. In a second known approach, termed endpoint nephelometry, the scattered light intensity is measured twice—first at the beginning of the reaction and again at the end of the reaction. Unfortunately, for some materials, the reaction time from beginning to end is unacceptably long—i.e. from several minutes to several hours or more. Consequently, after the initial scatter measurement is made, the sample container is removed from the nephelometer and placed in an incubation area where the reaction progresses toward completion. The nephelometer is thus freed in the interim for measuring other samples. When the reaction is complete, the container is then repositioned in the nephelometer for the final measurement.

It has been found that imperfections and variations in the sample container wall or window areas, such as scratches, bubbles, deformations, and the like, can introduce significant errors in the measurement of light scattered by the sample—typically by intercepting and attenuating or otherwise distorting light passing therethrough. In addition the nature and extent of these errors will vary from one container to the next. Moreover, the number and severity of imperfections will vary around the circumference of a single container, which causes the measured error for the single container to depend on the relative rotational orientation of the container within the optical system. This compounds the problem for the aforedescribed endpoint measurements, since the container could be and almost invariably is reinserted into the nephelometer for the second measurement at a different rotational orientation than it had been in for the first measurement. Consequently, the error in the measured scattered light signal will be different for the first measurement than for the second measurement on the same sample. Of course, this error difference could be eliminated by configuring the container or by employing a mechanical key integral with the container enabling container placement in the nephelometer in only one rotational orientation. However, this expedient would not reduce the measured error differences between different containers. Moreover, a primary reason for using the disposable, cylindrical glass containers described above is their economy, simplicity and convenience, and any increase in structural or mechanical complexity would reduce their attractiveness from this standpoint.

SUMMARY OF THE INVENTION

The present invention resides in photometric analysis apparatus which overcomes the disadvantages of prior systems by compensating for optical variations or imperfections in the container holding the sample for measurement. The system is simple in construction and operation and is readily adapted for use in existing photometric analyzers.

To the foregoing ends the invention in its broadest aspects contemplates means for rotatably supporting the sample container at a measuring station in a position intersecting an optical axis of optical detection means thereat and means for rotating the container during an optical measurement interval in a manner causing window areas of the container to rotate past the optical axis during the measurement interval. Container rotation is established at a speed sufficient to cause the detector means to effectively integrate the light exiting all window areas of the container viewed by the detection means during the measurement interval, thereby compensating for optical variations of the individual window areas.

By virtue of the foregoing arrangement the detected optical signal for a given sample and sample container is rendered insensitive to the rotational orientation of the container at the measuring station, and the error detected between different containers of the same type is minimized. The arrangement is thus particularly suited for receiving the cylindrical containers performing nephelometric sample assays and particularly assays (1) in which a given sample is measured in the same container at different times, (2) in which different containers are employed for each sample, or (3) in which a sample container is randomly oriented at the optical measuring station for measurement.

DESCRIPTION OF THE PREFERRED EMBODIMENT

Figure 1:
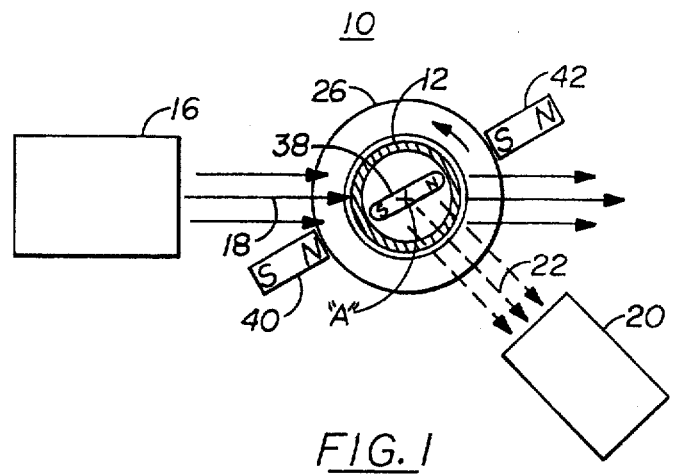
FIG. 1 is a top plan view of the measuring station of a nephelometer incorporating the present invention and illustrates in block diagram the optical excitation and the optical detection systems thereof.

As shown in the drawing for purposes of illustration, the invention is embodied in a nephelometer indicated generally by the numeral 10 which receives a sample container 12 at an optical measuring station 14 of the nephelometer. The sample container is illustrated as an optically transparent cylindrical glass shell vial, the nterior of which defines a chamber for receiving chemical reactants or other sample materials to be measured. Vials of this type are available in varying heights; a epresentative vial has an outside diameter of 9.0 mm and a wall thickness of 0.5 mm, and is obtainable from he Acme Glass Co. and the Brockway Glass Co. The ephelometer further includes an optical excitation ystem 16 for directing a beam of light along a predetermined axis 18 into the sample container and an optical letection system 20 for detecting light scattered by the contents of the container and passing therefrom along an optical axis 22. Axes 18 and 22 lie in a generally horizontal plane perpendicular to the vertical cylindrical axis "A" of sample container 12. Elements of the optical excitation and detection systems 16 and 18 are conventional and reference is made to the aforementioned patents for further details regarding these systems.

In accordance with a primary aspect of the present invention the sample container 12 is rotatably supported at the measuring station 14 in a manner allowing the container to be rotated about its vertical axis "A". To this end the bottom of container 12 is received within a well 24 of a generally circular supporting member 26 and is securely retained therein by an O-ring structure 28 which grips the outer circumference of the container. The O-ring itself seats within annular inwardly facing groove 30 in the vertical wall of well 24. The supporting member 26, in turn, is rigidly and coaxially affixed to the output shaft 32 of a drive motor 34. Motor 34 is secured to the main structural frame 36 of the nephelometer. Thus arranged motor 34 responds to signals from a system control (not shown) on command to rotate supporting element 26 and hence rotate the sample container 12 about its vertical axis A.

When the antigen and antibody reaction components are to be introduced into sample container 12, the optical excitation system 16 and the optical detection system 18 are appropriately enabled by the system control (not shown) in a conventional manner for the duration of the required optical measuring interval. For rate nephelometry, an optical measuring interval of up to one minute or so is established, during which time the optical detection means in the detection system 20 follows the increase in light scattered by the precipitate as the precipitate forms in the course of the antigen-antibody reaction. In endpoint nephelometry, by contrast, each of the two required measuring intervals may be much briefer, for example, only several seconds or so, since the scatter measurement of interest is simply the value of the scatter signal, and hence the amount of precipitate which exists, at a particular point in time.

For either case above, in accordance with an important aspect of the invention, motor 34 is energized to rotate sample container 12 during the optical measurement interval of interest while the detection system monitors the light scattered by the sample for assaying the sample. In this manner, the detection system 20 views the sample being assayed through all window areas in all rotational orientations of the sample container 12. Accordingly, the optical variations in the output scatter signal induced by imperfections and other variations in the different window areas of the container are averaged to derive a background error or base line error signal value which is essentially the same for all measurements with that particular container 12. Consequently, in endpoint analysis where a difference is taken between a final and an initial value of scattered light readings, the constant error in each reading will subtract out, so that the calculated difference will become independent of imperfections in each and between each container 12. Similarly, in rate analysis the constant error signal component of the total variable output scattered light signal is effectively subtracted since the derivative (rate) of a constant is zero. Thus, the invention renders the system insensitive to the various optical variations and imperfections in individual window areas of a container and between containers of the same type.

The speed at which container 12 must be rotated will depend on the nature of the imperfections in the container wall areas and on the nature of the sample being measured and the variation of the scattered light signal with time. For example, in rate measurements the scatter signal will increase with precipitate formation and the detection means must respond to the changing scatter signal with a time constant enabling the changing scatter signal to be accurately tracked. Also perturbations or noise is generated by the container optical imperfections as the container wall rotates past the detection system. Such noise pulses are superimposed on the basic sample scatter signal and should be of a sufficiently high frequency to be readily discriminated electronically from the sample scatter signal itself. For this reason, since the noise frequency is a function of rotational speed, it is desirable that the container be rotated at a speed substantially greater than the time constant of the detection system and preferably greater by about a factor of ten.

Figure 2:
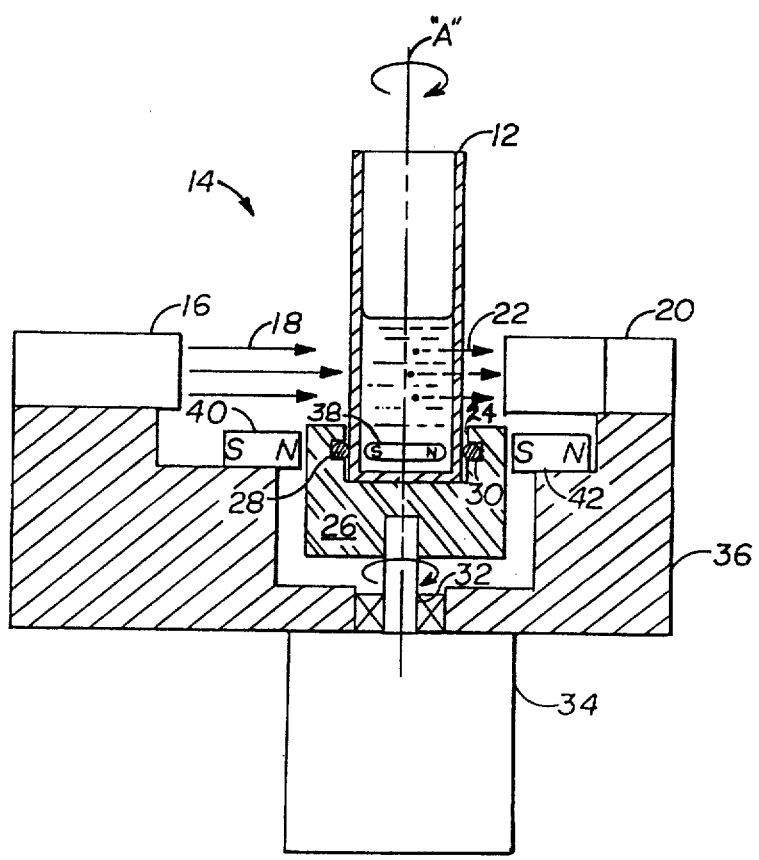
FIG. 2 is a view of the apparatus in FIG. 1 taken in a generally vertical plane through the measuring station.

FIGS. 1 and 2 further illustrate a cooperating arrangement for stirring the contents of the sample container 12 as the container rotates and during the optical measurement interval. The stirring arrangement includes a conventional magnetic stirring element 38, preferably a permanent magnet cylindrical rod or bar, horizontally disposed within the bottom of container 12. A pair of permanent magnets 40 and 42 are affixed to frame 36 outside of the container on opposite sides thereof in positions to be magnetically coupled to the stirring element. As illustrated in the figures, one magnetic pole of each external magnet 40 and 42 is aligned with respective opposite polarity magnetic pole of the stirring element. Thus arranged, the external magnets 40 and 42 establish a magnetic field restraining and holding the stirring element in a fixed horizontal position. Consequently, when drive motor 34 is actuated to rotate sample container 12, the container sample contents, which rotate together with the container, are stirred by relative motion of the sample material around and past the stationary stirring element.

While the external magnets retaining the stirring element 38 are illustrated as permanent magnet pole pieces 40 and 42, in an alternative form one or both pole pieces represent a switchable magnetic means, such as an electromagnet, which is manually or automatically switched on or off to enable or disable the magnetic field coupled to the stirring element. In this manner, with the field of the electromagnet switched on, the stirring element 38 is magnetically retained in its fixed horizontal position and operation of the system would be in a manner identical to that previously described. However, by switching the electromagnet off, the magnetic field is removed allowing the stirring element to move freely within the sample container 12 and hence to rotate along with the rotating container and its contents. This is desirable where, after the contents are stirred in the above described manner, it is preferred to optically or otherwise measure the container contents while the container rotates but without stirring taking place.

While the preferred embodiment of the invention has been illustrated in a nephelometric assay system, it will be apparent that the invention may be readily applied to other photometric systems such as spectrophotometric, fluorometric, bioluminescent, liquid scintillation, and the like, which are also subject to errors in optical measurements resulting from sample container optical variations or imperfections. Moreover, the invention may be adapted for sample containers having configurations other than cylindrical or having discrete window areas for light passage rather than the essentially infinite number of adjacent window areas of the cylindrical transparent vial employed herein. For example, a four-sided (square) container having four discrete windows is suitable for rotation at the measuring station. With such a container it would be desirable to modulate the light passing through the window areas with a conventional optical chopper or the like in a manner causing the detector to view the container contents at four spaced points in time for each revolution of the container, each point corresponding to alignment of a respective one of the four window areas with the detector optical axis. Moreover while a preferred embodiment of the invention has been illustrated and described, it will be apparent that modifications may be made therein without departing from the spirit and scope of the invention as defined in the appended claims.

What is claimed is:

1. In photometric analysis apparatus of the type having an optical measuring station at which a sample container holds sample material to be optically measured, the sample container including a plurality of window areas in a wall thereof for passing light into or out of the container during a measurement interval along one or more optical axes intersecting the measuring station, and optical detection means on one such axis for viewing the measuring station and operative during a measurement interval to monitor light exiting a window area of the container to develop an optical measurement of the sample within the container, the improvement characterized by:

means for rotatably supporting the sample container at the measuring station; and means for rotating the container during a measurement interval to cause the window areas thereof to rotate past the detection means at a rotational speed sufficient to cause the detection means to effectively integrate the light exiting the container through all window areas of the container thus viewed, thereby compensating for optical variations or imperfections in individual window areas of the sample container.

2. The apparatus of claim 1 wherein the container is a cylindrical vial supported for rotation about its cylindrical axis.

3. The apparatus of claim 1 or claim 2 including optical excitation means for directing a beam of light into the sample container, and wherein the optical detection means monitors light scattered by the container contents for performing nephelometric sample assays.

* * * * *